US009451375B2

(12) United States Patent
Maier

(10) Patent No.: US 9,451,375 B2
(45) Date of Patent: Sep. 20, 2016

(54) IMPLANTABLE MICROPHONE

(75) Inventor: Hannes Maier, Hamburg (CH)

(73) Assignee: Advanced Bionics AG, Staefa (CH)

(*) Notice: Subject to any disclaimer, the term of this patent is extended or adjusted under 35 U.S.C. 154(b) by 224 days.

(21) Appl. No.: 14/004,900

(22) PCT Filed: Mar. 17, 2011

(86) PCT No.: PCT/EP2011/054060
§ 371 (c)(1),
(2), (4) Date: Nov. 22, 2013

(87) PCT Pub. No.: WO2011/064410
PCT Pub. Date: Jun. 3, 2011

(65) Prior Publication Data
US 2014/0073842 A1    Mar. 13, 2014

(51) Int. Cl.
*H04R 25/00* (2006.01)
*A61N 1/36* (2006.01)

(52) U.S. Cl.
CPC ......... *H04R 25/606* (2013.01); *A61N 1/36032* (2013.01); *H04R 2225/67* (2013.01)

(58) Field of Classification Search
CPC ............ H04R 25/606; H04R 2225/67; A61N 1/36032
USPC ....................... 600/25; 607/57; 128/897–899
See application file for complete search history.

(56) References Cited

U.S. PATENT DOCUMENTS

| 5,859,916 | A | 1/1999 | Ball et al. |
| 6,093,144 | A | 7/2000 | Jaeger et al. |
| 6,554,761 | B1 | 4/2003 | Puria et al. |
| 7,214,179 | B2 | 5/2007 | Miller, III et al. |
| 7,556,597 | B2 | 7/2009 | Miller, III et al. |
| 7,840,020 | B1* | 11/2010 | Miller, III ............ H04R 25/604 381/326 |
| 2001/0031908 | A1* | 10/2001 | Buschek ............... H04R 25/606 600/25 |
| 2004/0039245 | A1 | 2/2004 | Jaeger et al. |
| 2005/0197524 | A1 | 9/2005 | Miller, III et al. |
| 2005/0222487 | A1* | 10/2005 | Miller, III ............ H04R 25/604 600/25 |
| 2006/0155346 | A1 | 7/2006 | Miller, III |
| 2007/0230721 | A1* | 10/2007 | White .................. H04R 19/005 381/166 |

FOREIGN PATENT DOCUMENTS

WO    WO-2007/001989    1/2007

OTHER PUBLICATIONS

International Search Report and Written Opinion received in International Application No. PCT/EP2011/054060 dated Jan. 3, 2012.

* cited by examiner

*Primary Examiner* — Navin Natnithithadha
*Assistant Examiner* — Sunita Reddy
(74) *Attorney, Agent, or Firm* — ALG Intellectual Property, LLC

(57) ABSTRACT

An implantable microphone, comprising a rigid housing, a sensor membrane for exposure to surrounding soft tissue, the sensor membrane being arranged to seal an opening of the housing, a transducer for generating an output signal corresponding to the deflection of the sensor membrane, and a compliant suspension arrangement located opposite to the sensor membrane for being exposed to soft tissue and for supporting the housing on soft tissue in a manner that the housing is moveable relative to said soft tissue upon acceleration of the housing and the soft tissue, the suspension arrangement comprising means for adjusting the spring constant of the suspension arrangement when the microphone is implanted.

12 Claims, 2 Drawing Sheets

IMPLANTABLE MICROPHONE

The invention relates to an implantable microphone, in particular for placement in soft tissue of a patient.

Fully implantable hearing instruments require biocompatibility and the possibility to implant all components of the device, in particular also the microphone. Typically, microphones are based on electromagnetic, electrostatic or piezoelectric detection of the deflection of a membrane of the microphone. Implantable microphones usually include a hermetic housing with a membrane facing the skin surface. In such microphones, a compliant membrane faces on one side tissue and on the other side an air filled interior of the housing, making it prone to accelerations perpendicular to the membrane. Various attempts for reducing such acceleration artifacts are known.

According to U.S. Pat. No. 5,859,916, US 2004/0039245 A1 and U.S. Pat. No. 6,093,144, some kind of perforated membrane is provided over the sensitive microphone area in order to reduce the mobility of the overlying tissue layer and thus its effective mass.

According to another approach to reduce acceleration effects on perceived sound as described in US 2005/0197524 A1 a soft damping material is inserted between the microphone housing and the underlying bone, thereby also reducing external forces acting on the microphone housing from the underlying bone of higher impedance.

U.S. Pat. No. 7,556,597 B1 relates to an approach wherein an implantable microphone is provided with an active damping mechanism which is operated according to a motion signal provided by a motion sensor included within the microphone housing.

US 2006/0155346 A1 relates to an implantable microphone comprising a motion sensor which provides for a motion signal which is taken into account in the processing of the microphone signal in order to reduce acceleration artifacts.

U.S. Pat. No. 7,214,179 B2 relates to an implantable microphone comprising an acceleration sensor for distinguishing acceleration forces from sound signals, wherein the output of the acceleration sensor is used to counteract or cancel the effects of acceleration in the output signal of the microphone membrane, which goal may be achieved pneumatically, mechanically, electrically analog and/or digitally. According to one embodiment, the acceleration sensor is a mass loaded cancellation membrane disposed inside the housing and parallel to the microphone membrane, wherein the mass loading allows the cancellation membrane to move in response to acceleration forces applied to the microphone housing.

WO 2007/001989 A2 relates to a microphone which is implanted in soft tissue at a location spaced from the surface of the patient's skull.

It is an object of the invention to provide for an implantable microphone with low sensitivity to vibration/acceleration and to bone conducted sound. It is also an object of the invention to provide for a corresponding hearing assistance method using such microphone.

According to the invention, these objects are achieved by an implantable microphone as defined in claim 1 and by a hearing assistance method as defined in claim 13, respectively.

The invention is beneficial in that, by providing for an adjustable suspension arrangement of the microphone housing, artifacts caused by acceleration of the tissue overlying the sensor membrane can be reduced in a particularly reliable manner, since the suspension arrangement can be adjusted according to the actual amount and mass of the tissue overlying the sensor membrane during or after implantation. In particular, due to such adjustment of the suspension arrangement, it is possible to approach the situation wherein in an acceleration situation the displacement of the microphone housing, as controlled by the suspension arrangement, with regard to the surrounding soft tissue equals the displacement of the membrane caused by acceleration of the overlying tissue, so that the net displacement of the sensor membrane due to acceleration is substantially zero.

Preferred embodiments of the invention are defined in the dependent claims.

Hereinafter, examples of the invention will be illustrated by reference to the attached drawings, wherein.

Figure 1:
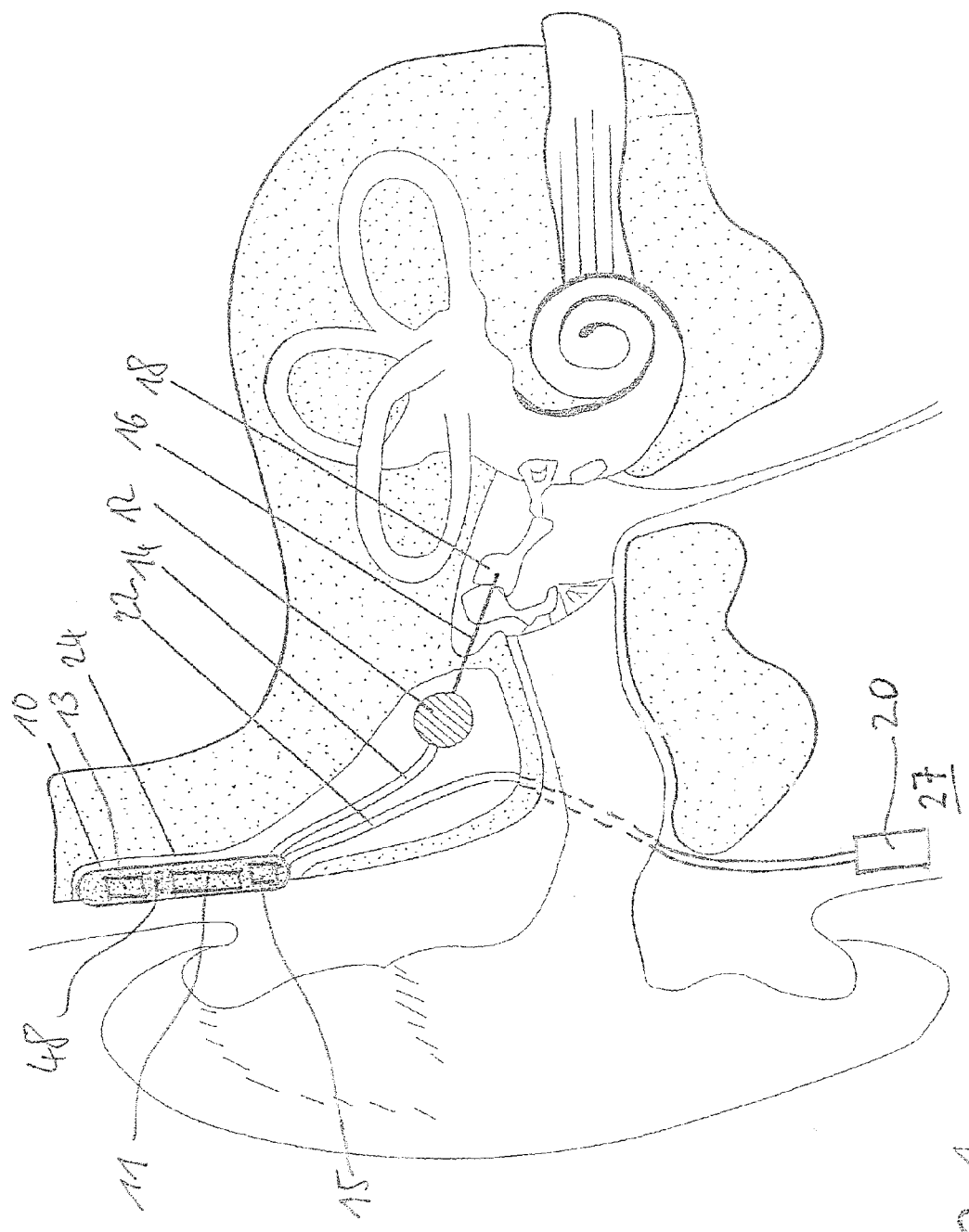
FIG. 1 is a cross-sectional view of an example of a hearing instrument using an implantable microphone according to the invention after implantation.

In the example shown in FIG. 1, a fully implantable hearing aid comprises an implanted housing 10, an implanted output transducer 12 which is connected via an implanted line 14 to the housing 10 and which may be designed as an electromechanical transducer for vibrating, via a mechanically coupling element 16, an ossicle 18, and an implanted microphone 20 connected via a line 22 to the housing 10.

The housing 10 is accommodated in an artificial cavity 24 created in the mastoid area and contains an audio signal processing unit 11, an electric power supply 13, a driver unit 15 and optionally components for wireless communication with a remote device. The power supply 13 typically includes an induction coil (not shown) for receiving electromagnetic power from a respective power transmission coil of an external charging device (not shown) and a rechargeable battery (not shown). Charging of the power supply 13 may be carried out during night when the user is sleeping.

The audio signal processing unit 11, which typically is realized by a digital signal processor, receives the audio signals captured by the microphone 20 and transforms them into processed audio signals by applying various filtering techniques known in the art. The processed audio signals are supplied to the driver unit 15 which drives the output transducer 12 accordingly, where they are transformed into a respective vibrational output of the transducer 12. Rather then being implemented as an electromechanical output transducer, the output transducer 12 could be any other known type of transducer, such as a floating mass transducer coupled to an ossicle, a cochlear electrode for electrical stimulation of the cochlear or an electrical or mechanical transducer acting directly on the cochlear wall, for example at the round window.

The microphone 20 preferably is placed in soft tissue 27 in a manner that it is completely surrounded by soft tissue, i.e. it neither touches a bone nor is it exposed to air.

Figure 2:
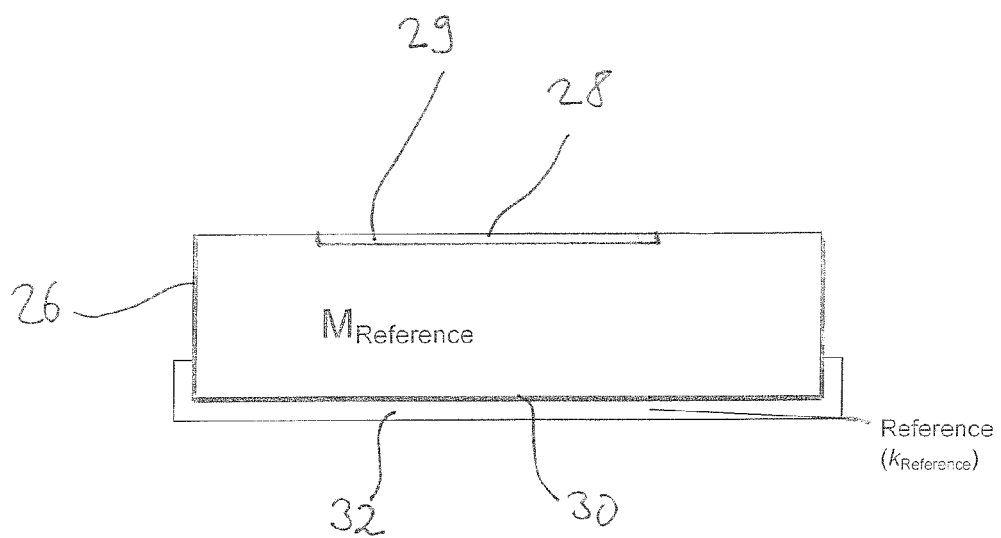
FIG. 2 is a cross-sectional view of a schematic example of an implantable microphone according to the invention.

A schematic example of the microphone 20 is shown in FIG. 2, wherein the microphone 20 comprises a rigid housing 26 having an opening sealed by a sensor membrane 28 and a rigid wall extending parallel and opposed to the membrane 28. The housing 26 may be made of titanium; also the membrane 28 may be made of titanium. The interior of the microphone 20 is hermetically sealed by the housing 26 and the membrane 28. Typically, the sensor membrane 28 is of circular shape, and the housing 26 has a circular cylindrical shape. The microphone 20 also comprises a transducer 29 for generating an output signal corresponding to the deflection of the sensor membrane 28. Such transducer 29 may be implemented, for example, as a piezoelectric element attached to the membrane 28 or as an optical sensor arrangement.

The microphone 20 also comprises a compliant suspension arrangement 32 located opposite to the sensor membrane 28 and exposed to soft tissue 27, which is provided for supporting the housing 26 on soft tissue 27 in a manner that the housing 26 is movable relative to the soft tissue 27 upon acceleration of the housing 26 and the soft tissue 27. The suspension arrangement comprises means for adjusting the spring constant $k_{Reference}$ of the suspension arrangement 32 when the microphone 20 has been implanted within the soft tissue 27.

Figure 3:
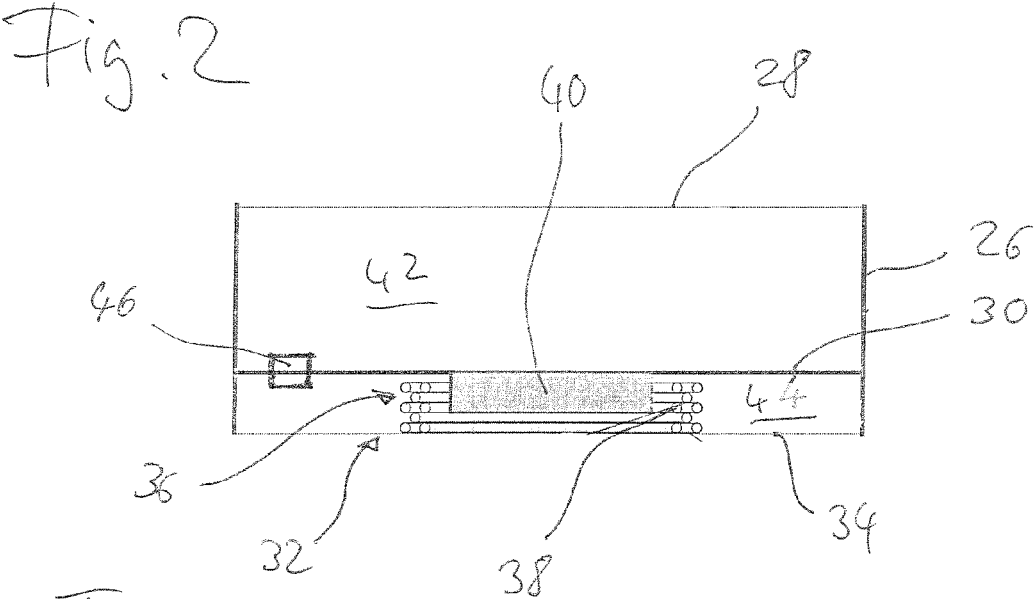
FIG. 3 is a view like FIG. 2, wherein two examples of the compliant suspension arrangement of the microphone of FIG. 2 are shown.

An example of the suspension arrangement 32 is illustrated in FIG. 3, wherein the suspension arrangement 32 comprises a reference membrane 34 arranged in parallel to the sensor membrane 28, with the reference membrane 34 being exposed to soft tissue 27 and being arranged to seal a further opening of the housing 26. The reference membrane 34 is arranged opposite to the sensor membrane 28.

In the example of FIG. 3, the suspension arrangement 32 comprises a compliant support arrangement 36 having a first end fixed at a rigid part 30 of the housing 26 and a second end fixed at a central region of the reference membrane 34, with the first end and the second end being movable relative to each other. In the example shown in FIG. 3, the support arrangement 36 is realized as an active magnetic damping element comprising a coil 38 and a magnetic core 40 actuated by the coil 38. In the example shown in FIG. 3, the coil 38 is fixed at the central region of the reference membrane 34, and the magnetic core 40 is fixed at the rigid part 30 of the housing 26 (of course, such arrangement could be reversed).

In the example shown in FIG. 3, the rigid part 30 of the housing 26 is an intermediate wall of the housing 26 which extends across the housing 26 parallel to the sensor membrane 28 and the reference membrane 34.

According to one embodiment, the spring constant $k_{Reference}$ of the suspension arrangement 32 may be adjusted by applying a certain appropriate current to the coil 38 in order to actuate the core 40 accordingly, i.e. to adjust the coupling force between the coil 38 and the core 40 accordingly. To this end, the line 22 may be used, and the implanted housing 10 may include respective control means 48.

According to an alternative embodiment, the rigid part 30 may separate a first internal cavity 42 comprising the sensor membrane 28 and having a first pressure from a second internal cavity 44 comprising the reference membrane 34 and the support arrangement 36 and having a second pressure. In this case, the housing 26 of the microphone 20 may comprise means for adjusting the gas pressure in the first internal cavity 42 and the gas pressure in the second internal cavity 44 in order to adjust the spring constant $k_{Reference}$ of the suspension arrangement 32. To this end, a valve 46 may be provided in the rigid part 30 for selectively exchanging gas between the first cavity 42 and the second cavity 44. This alternative embodiment does not require the presence of the compliant support arrangement 36.

The first approach has the advantage that it is very flexible and also allows to adapt dynamic properties, such as damping, to the properties of the overlying tissue 27; however, it requires permanent energy consumption of the magnetic damping element 36.

The second approach is beneficial in that it has no constant power requirement (the second approach does not require the presence of the active magnetic damping element 36). By regulating the pressure difference between the cavities 42 and 44 in a selective manner, both the spring constant $k_{ref}$ of the reference membrane 34 and the spring constant $k_{Membrane}$ of the sensor membrane 28 can be inversely modified when gas is transferred between the two cavities 42 and 44.

According to the present invention, a compliant suspension arrangement at the side opposite to the sensor membrane 28 is used which allows a compensation movement of the microphone body/housing 26 when accelerated. The microphone body provides a reference for the displacement of the sensor membrane 28. Both the tissue 27 overlying the sensor membrane 28 and the microphone housing 26 are equally subject to accelerations. The impression/deflection of the sensor membrane 28 may be compensated when the microphone housing 26 is used as an internal reference for the displacement of the sensor membrane 28 and moves the same distance as the sensor membrane 28 moves when the tissue 27 is accelerated. To obtain equal displacements at the sensor membrane 28 and the housing 26, the microphone housing 26 has to move in the direction of the displacement/impression of the sensor membrane 28 when the tissue 27 surrounding the microphone 20 is subject to accelerations.

When the microphone 20 is embedded in tissue 27, the movement of the microphone housing 26 is given by the force acting on the microphone housing 26 and the compliant/acoustic impedance of the underlying tissue 27. The equivalence of the displacement at constant acceleration is given by the force acting on the sensor membrane 28 and the force acting on the opposite side of the microphone 20. The latter is given by the sum of the force on the sensor membrane 28 and the force on the microphone housing 26. The condition to obtain equal displacements at the microphone side which is suitable to cancel out acceleration effects, leads to:

$$\Delta z_{Membrane} = \Delta z_{Reference}$$

$$\frac{\rho_{tissue} V_{tissue}(-\ddot{z})}{k_{Membrane}} = \frac{(\rho_{tissue} V_{tissue} + m_{Reference})(-\ddot{z})}{k_{Reference}}$$

where $V_{tissue}$ and $\rho_{Tissue}$ are the volume and density of the overlying tissue, $m_{Reference}$ the mass of the microphone. $k_{Reference}$ and $k_{Membrane}$ are the compliances of the microphone suspension and the microphone membrane describing the displacements of the microphone membrane and the body analog to:

$$k\Delta z = m\ddot{z} = f_z$$

The elastic properties of the sensor membrane 28, the mass of the microphone 20 and the density of the tissue 27 can be assumed to be constant and known prior to implantation, whereas the thickness of the tissue layer overlying the microphone depends on the implantation process and is not exactly known prior to implantation. Also, the thickness of the overlying tissue layer may be subject to long-term changes as well as short-term changes (for example, due to regulation of the blood flow). Moreover, the elastic properties of the overlying tissue layer may change in time.

According to the present invention, the spring constant of the suspension arrangement 32 is adjusted in such a manner that the above balance condition of equal displacements of the sensor membrane 28 and the microphone housing 26 is fulfilled. In order to take into account also the thickness and the elastic properties of the tissue layer overlying the microphone 20, which are not exactly known prior to implantation, the suspension arrangement 32 is designed such that the spring constant of the suspension arrangement 32 may be adjusted at least once even after implantation of the microphone 20.

According to one embodiment, an active magnetic damping element 36 is provided which can be dynamically adjusted by changing the current through the coil 38. According to an alternative embodiment, the pressure in the first cavity 42 sealed by the sensor membrane 28 and the pressure in the second cavity 34 sealed by the reference membrane 34 may be adjusted.

The invention claimed is:

1. An implantable microphone, comprising:
a rigid housing, a sensor membrane configured for exposure to surrounding soft tissue, the sensor membrane being configured to seal an opening of the housing,
a transducer for generating an output signal corresponding to a deflection of the sensor membrane, and
a compliant suspension arrangement located opposite to the sensor membrane, the compliant suspension arrangement configured for exposure to the surrounding soft tissue and for supporting the housing on the surrounding soft tissue in a manner that the housing is moveable relative to the surrounding soft tissue upon acceleration of the housing and the surrounding soft tissue, the suspension arrangement configured to adjust a spring constant of the suspension arrangement and comprising a reference membrane arranged in parallel to the sensor membrane, the reference membrane configured for exposure to the surrounding soft tissue and to seal a further opening of the housing.

2. The microphone of claim 1, wherein the suspension arrangement comprises a compliant support arrangement having a first end fixed at a rigid part of the housing and a second end fixed at a central region of the reference membrane, with the first end and the second end being moveable relative to each other.

3. The microphone of claim 2, wherein the support arrangement comprises an active magnetic damping element comprising a coil and a magnetic core actuated by the coil.

4. The microphone of claim 3, wherein the magnetic core is fixed at said rigid part of the housing and the coil is fixed at the central region of the reference membrane.

5. The microphone of claim 3, further comprising means for applying a current to the coil in order to adjust the spring constant of the suspension arrangement.

6. The microphone of claim 3, further comprising means for controlling current through the coil in order to adjust a damping constant of the suspension arrangement.

7. The microphone of claim 2, wherein said rigid part of the housing is an intermediate wall of the housing.

8. The microphone of claim 7, wherein the intermediate wall extends across the housing and parallel to the sensor membrane.

9. The microphone of claim 1, wherein an intermediate wall of the housing separates a first internal cavity comprising the sensor membrane and having a first gas pressure from a second internal cavity of the housing comprising the reference membrane and having a second gas pressure.

10. The microphone of claim 9, wherein the housing contains means for adjusting the first gas pressure and the second gas pressure in order to adjust the spring constant of the suspension arrangement.

11. The microphone of claim 10, wherein the pressure adjusting means comprises a valve for exchanging gas between the first cavity and the second cavity.

12. A fully implantable hearing instrument comprising:
a microphone comprising
a rigid housing, a sensor membrane configured for exposure to surrounding soft tissue, the sensor membrane being configured to seal an opening of the housing,
a transducer for generating an output signal corresponding to a deflection of the sensor membrane, and
a compliant suspension arrangement located opposite to the sensor membrane, the compliant suspension arrangement configured for exposure to the surrounding soft tissue and for supporting the housing on the surrounding soft tissue in a manner that the housing is moveable relative to the surrounding soft tissue upon acceleration of the housing and the surrounding soft tissue, the suspension arrangement configured to adjust a spring constant of the suspension arrangement and comprising a reference membrane arranged in parallel to the sensor membrane, the reference membrane configured for exposure to the surrounding soft tissue and to seal a further opening of the housing; and
an audio signal processing unit configured to process the output signal and an output transducer for stimulating a patient's hearing according to the output signal processed by the audio signal processing unit.

* * * * *